United States Patent [19]

Hanahan et al.

[11] Patent Number: 4,551,446

[45] Date of Patent: Nov. 5, 1985

[54] USE OF SYNTHETIC PHOSPHOGLYCERIDES POSSESSING PLATELET ACTIVATING PROPERTIES AS DESENSITIZING AGENTS

[75] Inventors: Donald J. Hanahan; R. Neal Pinckard, both of San Antonio, Tex.

[73] Assignee: Board of Regents, The University of Texas System, Austin, Tex.

[21] Appl. No.: 453,224

[22] Filed: Dec. 27, 1982

Related U.S. Application Data

[60] Continuation-in-part of Ser. No. 349,699, Feb. 18, 1982, Pat. No. 4,504,474, which is a division of Ser. No. 163,808, Jun. 27, 1980, Pat. No. 4,329,302.

[51] Int. Cl.$^4$ ................. A61K 31/685; A61K 31/66; C07F 9/28
[52] U.S. Cl. .................................... 514/77; 260/403; 260/925; 260/944; 260/945; 514/114
[58] Field of Search ............... 260/403, 925, 944, 945; 424/199, 211; 514/77, 114

[56] References Cited

FOREIGN PATENT DOCUMENTS 54-106430  8/1979  Japan ................... 260/403

OTHER PUBLICATIONS

*Chemical Abstracts*, vol. 94, No. 13 (Mar. 30, 1981), p. 568, abstract No. 101,206t, Halonen, Marilyn et al., "Resp. & Cir. Alterations Induced by AGEPC, a Mediator of IgE Anaphylaxis in the Rabbit".
*Chemical Abstracts*, vol. 93, No. 7, (Aug. 18, 1980), pp. 84–85, abstract No. 61,491c, McManus, Linda M. et al., "Pathobio. of the I.V. Infusion of AGEPC, a Synthetic PAF, in the Rabbit.
*C. R. Acad. Sc. Paris*, t. 289 (Nov. 26, 1979), Serie D, No. 14, pp. 1037–1040, Benveniste et al., "Synthesis and Proposed Structure for Platelet Activating Factor".
*Biochemical and Biophysical Research Communications*, vol. 90, No. 4 (Oct. 29, 1979), pp. 1194–1200, Blank et al., "Antihypertensive Activity of an Alkyl Ether Analog of Phosphatidylcholine".
*J. of Immunology*, vol. 123, No. 4 (Oct. 1979), pp. 1847–1857, Pinckard et al., "Physicochemical & Functional Identity of Rabbit PAF Released in vivo During IgE Anaphylaxis with PAF released in vitro from IgE Sensitized Basophils".
*J. of Biological Chemistry*, vol. 254, No. 19 (Oct. 10, 1979), pp. 9355–9358, Demopoulos et al., "Platelet-Activating Factor".

*Primary Examiner*—Thomas A. Waltz
*Attorney, Agent, or Firm*—Arnold, White & Durkee

[57] ABSTRACT

Novel synthetic glyceryl-phosphorylcholine compounds are prepared having biological activity paralleling that of naturally generated platelet activating factor. In particular, the novel compounds of the present invention are useful to induce specific desensitization or tachyphylaxis of certain cells and tissues to platelet activating factor, rendering the cells or tissue unresponsive or hyporesponsive to subsequent platelet activating factor stimulation.

2 Claims, No Drawings

USE OF SYNTHETIC PHOSPHOGLYCERIDES POSSESSING PLATELET ACTIVATING PROPERTIES AS DESENSITIZING AGENTS

The Government has rights in the invention pursuant to National Institute of Health Grant No. HL-22555 awarded by the Department of Education and Welfare.

This is a continuation in part application of application Ser. No. 349,699 filed Feb. 18, 1982 and now U.S. Pat. No. 4,504,474 which is a division of application Ser. No. 163,808, filed June 27, 1980, now issued as U.S. Pat. No. 4,329,302, May 11, 1982.

This invention relates to synthetic phosphoglyceride compounds, to methods of preparing such compounds, and to the use of such compounds in mediating platelet activation.

Applicants have discussed background information relative to their invention in papers entitled "Platelet Activating Factor," 254 *Journal of Biological Chemistry* 9355–9358 (1979) and "Physicochemical and Functional Identity of Rabbit Platelet-Activating Factor (PAF) Released In Vivo During IgE Anaphylaxis with PAF Released In Vitro from IgE Sensitized Basophils," 123 *Journal of Immunology* 1847–1857 (1979). In Applicants' papers the elucidation of functional and physicochemical properties of PAF were explored.

The platelet, now recognized as an important cellular element involved in the acute inflammatory process, has been strongly implicated in a variety of immunologically mediated forms of tissue injury including immune complex deposition and IgE induced systemic anaphylactic shock. Platelet participation in these disease processes likely involves a cooperative cellular interaction where antigen stimulated IgE-sensitized basophils and presumably mast cells release a chemical mediator, platelet activating factor (PAF) which in turn interacts with the platelets inducing aggregation and secretion of granular constituents. As a further consequence of platelet activation there may result a fatal reaction consisting of acute pulmonary hypertension, right heart dilation, systemic hypotension, significant increases in total pulmonary resistance, decreases in dynamic lung compliance and often complete pulmonary apnea.

The existence of a platelet activating factor was proposed in an article by Henson, P.M., 131 *Journal of Experimental Medicine* 287 (1970). Heretofore, the definition of its chemical structure and biochemical activity was not achieved due to the limited quantities of material available for study.

One of the early reports on the chemical nature of PAF was that of Benveniste, J., 249 *Nature* 581 (1974). In this communication, Benveniste reported physicochemical characteristics of PAF to include a molecular weight of approximately 1100, a pI near 10 and an ability to bind to bovine serum albumin. A later study by Benveniste, J., et al, 269 *Nature* 170 (1977) reported the purification of PAF isolates by successive thin layer chromatography with chloroform: methanol: acetic acid: water as the solvent system. On the basis of a spray reaction, they concluded that PAF was a phospholipid.

Other studies exploring the physico-chemical characteristics of PAF suggested that PAF was a relatively small molecule having a molecular weight ranging from 300–500 daltons. Additionally, data suggested it was stable to freezing, stable to heating at 56° C. for 30 minutes, and stable at pH 3–10. No significant destruction by periodate, 2-mercaptoethanol and trypsin was noted, indicating PAF's resistance to oxidation, reduction and enzymatic attack respectively.

As more researchers released their findings certain inconsistencies became evident. For example the proposed molecular weight of PAF ranged from 300 to 1100 daltons. Moreover, one research group reported that PAF was inactivated by phospholipase D while another group reported suppression of PAF by phospholipase A and C but not by phospholipase D.

SUMMARY OF THE INVENTION

This invention relates to phosphoglycerides which exhibit platelet activating factor properties.

The invention contemplates a class of phosphoglycerides, particularly 1-0-alkyl ether phosphoglycerides and 1-0-fatty acyl phosphoglycerides (lysolecithin derivatives), which exhibit extremely potent biological activity towards washed rabbit platelets. The most active compound is 1-0-alkyl-2-acetyl-sn-glyceryl-3-phosphorylcholine (AGEPC), which demonstrates a biological activity indistinguishable from that of naturally generated rabbit platelet activating factor. Its biochemical and biological properties so closely parallel those of naturally occurring PAF, that it is proposed they are one and the same compound. Subsequent research by the Applicants has confirmed that AGEPC and PAF are the same composition (Hanahan et al., 255 *J. Biol. Chem.* 5514–5516 (June 1980). The propionyl derivative of the ether glyceride series is nearly as potent, but the butyryl and longer chain fatty acid derivatives have relatively little or no activity. Comparable derivatives of the lysolecithin series, while having activity toward platelets, have significantly lower potency than the ether glyceride series.

The synthetic phosphoglycerides which are the subject of this invention are represented generally by the formula:

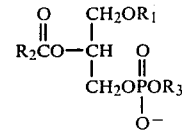

wherein $R_1$ is a long chain carbonyl

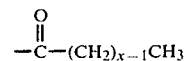

or a long chain alkyl —$(CH_2)_xCH_3$, wherein x denotes the integer 15 or 17; $R_2$ is a lower alkyl such a methyl, ethyl, or n-propyl; and $R_3$ is choline or amine bases thereof, such as

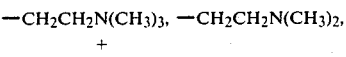

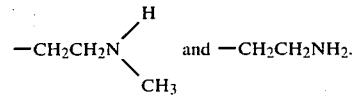

The glyceride compounds of this invention are useful in the modulation of physiological activity in host systems. In particular, these compounds are useful in inducing the specific desensitization or tachyphylaxis of certain cells and tissues to subsequent challenge to platelet activating factors.

DETAILED DESCRIPTION OF THE PREFERRED EMBODIMENT

The following discussion is in terms of the preferred embodiments of this invention, which represent the best mode known to the inventors at the time of this application.

In accordance with the preferred embodiments of this invention a series of synthetic phosphoglycerides were developed having biological and biochemical characteristics analogous to endogenous PAF. The strategy culminating in the invention utilized the base sensitivity of PAF to investigate its possible resynthesis from the degradation products. The investigation revealed the acetylation of the products derived from base treatment of endogenous PAF produced a compound with high biological activity and an $R_f$ indistinguishable from that of the native PAF. Further, it was discovered that small chain acylation ($C_2$, $C_3$, $C_4$) of 1-acyl-sn-glyceryl-3-phosphorylcholine (lysolecithin) gave rise to glyceryl acyl phospholipids derivatives with platelet-activating behavior. While these lysolecithin derivatives functionally mimicked PAF, certain physiochemical properties differentiated and excluded them as being the native PAF molecule.

Further in accordance with such embodiments, small chain acylation ($C_2$, $C_3$, $C_4$) of the glyceryl ether phosphorylcholine, 1-0-alkyl-sn-glyceryl-3-phosphorylcholine, produced a class of glyceryl ether phospholipid chemical mediators having molar activities magnitudes of order greater than the lysolecithin derivatives. More particularly, acetylation of the precursor glyceryl ether phosphorylcholine yielded an exquisitely high activity platelet activating compound with biochemical properties identical to PAF. On the basis of further biochemical and functional tests to be discussed in the examples, Applicants' proposed and subsequently proved that 1-0-alkyl-2-acetyl-sn-glyceryl-3-phosphorylcholine (AGEPC) is structurally and biologically identical to native PAF.

According to the process of the present invention naturally occurring precursors easily isolated in high purity are subjected to base catalyzed methanolysis and subsequent reacylation for final synthesis of AGEPC and related compounds. More specifically, glyceryl ether phosphorylcholine obtained by hydrogenation of vinyl ether phosphorylcholine is subjected to base-catalyzed methanolysis, and subsequent reacylation utilizing low molecular weight acid anhydrides ($C_2$, $C_3$, $C_4$). Alternatively, lysolecithin derived from phospholipase $A_2$ treatment to egg lecithin is also subjected to acylation using low molecular weight acid anhydrides ($C_2$, $C_3$, $C_4$) forming a series of lysolecithin derivatives exhibiting platelet activating properties. The resulting series of synthetic phosphoglycerides which exhibit platelet activating properties are represented by the formula:

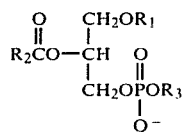

wherein $R_1$ is a long chain carbonyl

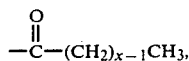

or a long chain alkyl, $-(CH_2)_x CH_3$, wherein x denotes the integer 15 or 17; $R_2$ is a lower alkyl such as methyl, ethyl, or n-propyl; and $R_3$ is choline or amine base thereof selected from the group consisting of

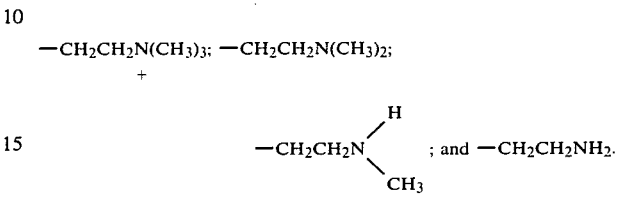

Of particular importance in the synthesis of biochemical mediators is that the process yields a stereochemically well defined product. In the present invention, the utilization of naturally occurring precursors ensures the optically pure configuration needed to accommodate many biochemically mediated reactions.

Isolation and purification of the purcursors, lysolecithin and vinyl ether-containing phospholipids have been described respectively in Wells, M.A., and Hanahan, D.J., 8 Biochemistry 414 (1969) and Pugh, E.L., et al., 18 Journal of Lipid Research 710 (1977).

Preparation and purification of endogenous PAF is described in Applicants' papers 254 Journal of Biological Chemistry 9355 (1979), 123 Journal of Immunology 1847 (1979), and 255 Journal of Biological Chemistry 5514–5516 (June 1980).

The preferred embodiments of this invention are better illustrated by the examples which follow. In the examples the following materials and procedures were employed.

All solvents were ACS reagent grade or of the highest purity available. Acetic anhydride (99.7%) was a product of Fisher Scientific Co., propionic anhydride (97%) and butyric anhydride (99%) were purchased from Aldrich Chemical Co. Crystalline bovine serum albumin was obtained from Miles-Pentex.

Organic phosphorus was determined by the method of Bartlett, G., 234 Journal of Biochemistry 466 (1950). Gasliquid chromatography was conducted on a Varian model 3700 gas chromatograph equipped with a 2 m × ⅛ inch outer diameter stainless steel column containing 15% DEGS on Chromosorb AW 80/100. The temperature conditions were: column, 180° C.; flame ionization detector, 230° C.; and inlet, 220° C. Infrared spectra were obtained on a Beckman IR 4230 recording spectrophotometer using 1 mm NaCl cells.

Tyrode's, pH 7.2 was a buffer composed of 8 g/liter NaCl; 0.195 g/liter KCl; 1.02 g/liter $NaHCO_3$; 0.213 g/liter $MgCl_2.6H_2O$; 1.00 g/liter D-glucose; and 2.50 g/liter gelatin. The buffer was adjusted to pH 7.2 and contained 0.145 g/liter $CaCl_2$ (anhydrous).

In the following examples, Examples 1–6 illustrate the preferred methods of preparation of the subject composition invention. More particularly, Examples 1–3 describe the synthesis of the alkyl ether glyceride series while Examples 4–6 describe the synthesis of the fatty acyl glyceride (lysolecithin) series. Examples 7–15 depict a physiochemical (chromatographic migration) relationship among the invented synthetic phosphoglycerides and endogenous PAF. Further, Examples 16-26 describe various tests illustrating the applied uses of the novel series of phosphoglycerides.

EXAMPLE 1

Preparation of 1-0-alkyl-2-acetyl-sn-glyceryl-3phosphorylcholine (AGEPC)

Vinyl ether-containing phospholipids of fresh beef heart were isolated and purified as outlined by Pugh et al, 18 *J. Lipid Res.* 710–716 (1977). Briefly, a fresh beef heart was cut up and coarsely ground. Meat was homogenized with methanol: choloroform (2:1 v/v) for 1 minute. The mixture was filtered and the filtrate was subjected to phase separation, using chloroform: water (1:1 v/v). The chloroform phase was concentrated in vacuo to dryness. The residual lipid material from the chloroform layer was dissolved in chloroform (50 ml) and stored at 4° C. The yield of total lipids was approximately 19.9 mg/g fresh tissue.

The choline containing fraction was further purified by thin layer chromatography using preparative (Analtech) Silica Gel G 1000μ plates developed in a chloroform: methanol: water (65:35:6 v/v) solvent system.

The purified choline fraction was recovered by scraping the appropriate segment of the TLC plate and eluting the adsorbed choline fraction with chloroform: methanol: water (1:2:0.8 v/v). A portion of the eluted choline fraction was subjected to catalytic hydrogenation using $PtO_2$ as a catalyst at a hydrogen pressure of 60 p.s.i. for a period of three hours at room temperature. The resulting mixture of completely saturated choline containing phospholipids gave no reaction to Schiff base reagent indicating the absence of vinyl ethers or plasmalogens.

Further, the resulting mixture of completely saturated phosphorylcholines was subjected to short term base-catalyzed methanolysis, involving deacylation of the 2-glyceryl position in a chloroform-methanolic alkali medium. Specifically, the completely saturated phosphorylcholine mixture was treated with 0.5 N NaOH in a methanol-chloroform mixture (10:1 v/v) for 2–3 minutes at 10° C. The reaction was quenched and neutralized by adjusting the reaction mixture to pH 7.

The resulting glyceryl ether phospholipid, 1-0-alkyl-sn-glyceryl-3-phosphorylcholine, was isolated by thin layer chromatography ($R_f$ 0.15) using a solvent system of chloroform: methanol: water (65:35:6 v/v). The isolated substrate contained 5.1% phosphorus and exhibited the following infrared pattern: 2930 cm$^{-1}$, 2860 cm$^{-1}$, 1460 cm$^{-1}$, 1375 cm$^{-1}$, —$CH_2$ and —$CH_3$; 1090 cm$^{-1}$, P—O; 1060 cm$^{-1}$, P—O—C; 968 cm$^{-1}$, P—O—choline. The glyceryl ether composition (mole percent) was determined by gas-liquid chromatography wherein the ether linkage alkyl chain length was found to be 16:0 (78%) and 18:0 (22%).

Reacylation of the glyceryl ether analog was accomplished by dissolving the glyceryl ether analog in chloroform and adding acetic acid anhydride in a ratio of one part ether substrate and five parts acid anhydride. Addition of catalytic amounts of perchloric acid allowed complete acetylation in 45 seconds at room temperature. Separation of the reaction product, 1-0-alkyl-2-acetyl-sn-glyceryl-3-phosphorylcholine (AGEPC), was achieved through phase separation by mixing chloroform, methanol, and water with the reaction mixture. The chloroform rich layer containing the AGEPC was washed with methanol: water (10:9 v/v) until the chloroform layer was acid free. The product AGEPC and amine bases thereof was further purified by thin layer chromatography using chloroform: methanol: water (65:35:6 v/v).

EXAMPLE 2

Preparation of 1-0-alkyl-2-propionyl-sn-glyceryl-3-phosphorylcholine

Example 1 was repeated except that the specific anhydride used in the reacylation process was propionic acid anhydride.

EXAMPLE 3

Preparation of 1-0-alkyl-2-butyryl-sn-glyceryl-3-phosphorylcholine

Example 1 was repeated except that the specific anhydride used in the reacylation process was butyric acid anhydride.

EXAMPLES 4–6

Preparation of Lysolecithin Derivatives

Lysolecithin (1-acyl-sn-glyceryl-3-phosphorylcholine) and amine bases thereof were prepared through action of phospholipase $A_2$ on purified egg lecithin. Lysolecithin was recovered as a single band ($R_f$ 0.15) by thin layer chromatography using a solvent system of chloroform: methanol: water (65:35:6 v/v). Chemical analysis of the lysolecithin showed it contained 5.52% phosphorus and had an infrared spectrum with the following bands: 2925 cm$^{-1}$, 2855 cm$^{-1}$, 1458 cm$^{-1}$, —$CH_3$ and —$CH_2$; 1730 cm$^{-1}$, ester C=O; 1082 cm$^{-1}$, P—O—; 1055 cm$^{-1}$, P—O—C; 965 cm$^{-1}$ P—O—choline. Its fatty acid composition (mole percent) as determined by gas liquid chromatography was 16:0 (68%), 18:0 (27%) and 18:1 (4%).

Acylation of lysolecithin was accomplished by the acylation procedure outlined in Example 1 wherein a specific anhydride was reacted with the substrate, lysolecithin and amine bases thereof. The products are tabulated below.

| Example | Specific Acid Anhydride | Product |
| --- | --- | --- |
| 4 | acetic acid anhydride | 1-acyl-2-acetyl-sn-glyceryl-3-phosphorylcholine and amine bases thereof |
| 5 | propionic acid anhydride | 1-acyl-2-propionyl-sn-glyceryl-3-phosphorylcholine and amine bases thereof |
| 6 | butyric acid anhydride | 1-acyl-2-butyryl-sn-glyceryl 3-phosphorylcholine and amine bases thereof |

The phosphorus content of the acetyl, propionyl, and butyryl derivatives ranged from 5.50 to 5.10%.

EXAMPLES 7–15

Chromatographic Comparison of Synthetic Phosphoglycerides with Endogenous PAF After the compounds in Examples 1–6 were synthesized, their behavior as compared to endogenous platelet activating factor (PAF) was studied through application on thin layer chromatography. These samples were developed for 50 minutes on a precoated Silica Gel G plates (250μ) (Analtech) in a solvent system of chloroform: methanol: water (65:35:6 v/v). The spots were visualized by spraying the plate with concentrated sulfuric acid and charring.

Results were as follows:

| Example | Compound | $R_f$ |
|---|---|---|
| 7 | endogenous PAF (control) | 0.21 |
| 8 | 1-O—alkyl-2-acetyl-sn-glyceryl-3-phosphorylcholine | 0.21 |
| 9 | 1-O—alkyl-2-propionyl-sn-glyceryl-3-phosphorylcholine | 0.24 |
| 10 | 1-O—alkyl-2-butyryl-sn-glyceryl-3-phosphorylcholine | 0.30 |
| 11 | 1-acyl-2-acetyl-sn-glyceryl-3-phosphorylcholine | 0.21 |
| 12 | 1-acyl-2-proprionyl-sn-glyceryl-3-phosphorylcholine | 0.25 |
| 13 | 1-acyl-2-butyryl-sn-glyceryl-3-phosphorylcholine | 0.26 |
| 14 | lysolecithin (control) | 0.15 |
| 15 | sphingomyelin (control) | 0.23 |

Both the 1-0-alkyl-2-acetyl-sn-glyceryl-3-phosphorylcholine (AGEPC) and 1-acyl-2-acetyl-sn-glyceryl-2-phosphorylcholine (AcLL) migrated the same distance ($R_f$) as endogenous PAF. Each of the other derivatives has increasing $R_f$ values relative to the increasing 2-acyl-carbon length.

EXAMPLES 16–22

Comparison of Functional Activity of Endogenous PAF and Synthetic Phosphoglycerides A series of experiments were performed demonstrating the biological activities of the various synthetic phosphoglycerides with respect to their ability to induce dose-dependent platelet activation, as evidenced by platelet shape change without aggregation, platelet aggregation without serotonin secretion, and irreversible platelet aggregation with 50% secretion of serotonin (the latter measurement being defined as 1 unit of PAF-like activity).

The following procedure was employed to assess dose-dependent platelet activation as expressed by the various test parameters listed above. Preparation of washed $^3$H-serotonin-labeled rabbit platelets is described in Applicants' paper, 123 *Journal of Immunology* 1847 (1979).

Rabbit platelets internally labeled with $^3$H-serotonin (New England Nuclear; 28.2 Ci/mmol) were washed on FicollPaque cushions and adjusted to $2.5 \times 10^8$ platelets/ml of Tyrode's buffer, pH 7.2. Appropriate dilutions of PAF or the test analogs were prepared in pyrogen-free 0.15 M NaCl containing 2.5 mg/ml of crystalline bovine serum albumin (albumin was required for PAF and test analog dispersion). Four microliters of the various dilutions of PAF and test analogs were added to 200μl of prewarmed (37° C.) $^3$H-serotoninlabeled platelets in plastic test tubes. After the 60 second incubation, 20 μl of cold 1.5 M formaldehyde were added to stop the reactions. The plastic test tubes were immediately cooled to 0° C., centrifuged at 2200×g for 10 min. and the supernatants were assayed for percentage of $^3$H-serotonin secretion relative to 100% controls prepared by the addition of Triton X-100 (a nonionic detergent which induces complete non-specific rupture of platelets) to 200 μl of the starting platelet suspension.

The percentage of serotonin secretion was determined by liquid scintillation spectroscopy relative to that released from the same volume of platelets after the addition of 10 μl of 2.5% triton X-100. The results were graphed linearly as the percent serotonin secretion versus the volume of test sample added. A 50% serotonin secretion endpoint was chosen to define 1 unit of PAF activity. Results of test samples were listed as molar concentration (mean±standard deviation) equivalent to 1 functional unit of PAF activity. One unit of PAF activity was equivalent to $1 \times 10^{-10}$ M PAF.

Platelet aggregation and platelet shape change were both determined utilizing a Chronolog aggregometer at 37° C. with stirring (1200 rpm) of the washed rabbit platelets and test sample mixture (500 μl, 250,000 platelets/μl). The endpoint standard defined as the amount of test sample which resulted in a 50% increase in light transmission, as measured by the aggregometer.

Moreover, the platelet shape change with no aggregation was also determined according to the technique above. Since these test reactions are dose dependent, varying the concentration of test sample will produce a different platelet reaction. At the lowest concentration range of activity a test compound induces a platelet shape change, characterized by the platelet changing from the normal elliptical configuration to a spherical configuration. When rotated on a central axis the normal elliptical platelet will allow light to pass similar to a strobe effect. However as the platelet changes to a circular configuration there is a decrease in light transmittance. It is this decrease in light transmittance which is assigned the endpoint of platelet shape change activity.

Results were as follows:

| Example | Compound | $^3$H—Serotonin release, 50%; M × $10^{-10}$ (mean ± stan. deviation) | Aggregation M × $10^{-10}$ | Shape Change M × $10^{-10}$ |
|---|---|---|---|---|
| 16 | PAF | 1.0 | 0.3 | 0.1 |
| 17 | 1-O—alkyl-2-acetyl-sn-glyceryl-3-phosphorylcholine | 1.0 ± 0.3 | 0.3 | 0.1 |
| 18 | 1-O—alkyl-2-propionyl-sn-glyceryl-3-phosphorylcholine | 1.4 ± 0.4 | 0.3 | 0.1 |
| 19 | 1-O—alkyl-2-butyryl-sn-glyceryl-3-phosphorylcholine | 7.0 ± 2.0 | 10 | 6 |
| 20 | 1-acyl-2-acetyl-sn-glyceryl-3-phosphorylcholine | 240 ± 50 | 80 | 40 |
| 21 | 1-acyl-2-propionyl sn-glyceryl-3-phosphorylcholine | 300 ± 60 | 70 | 30 |
| 22 | 1-acyl-2-butyryl-sn-glyceryl-3- | Not active | Not Active | Not Active |

| Example | Compound | $^3$H—Serotonin release, 50%; M × $10^{-10}$ (mean ± stan. deviation) | Aggregation M × $10^{-10}$ | Shape Change M × $10^{-10}$ |
|---|---|---|---|---|
| | phosphorylcholine | | | |

EXAMPLE 23

Native PAF and 1-O-alkyl-2-acetyl-sn-glyceryl-3-phosphorylcholine were utilized in cross-desensitization experiments to evaluate functional similarities. These experiments were based upon the observations that exposure of platelets to PAF under nonsecreting conditions (i.e., in absence of extracellular calcium) desensitized the platelets to a second exposure to PAF in the presence of calcium. The desensitization is stimulus specific since serotonin secretion induced by other platelet stimulators not related to PAF, e.g., collagen or thrombin, was not decreased. Thus, platelets were desensitized to native PAF, AcLL or to AGEPC, and secretion profiles were determined upon control and desensitized platelets utilizing the native PAF, the synthetic phosphoglycerides, collagen and purified thrombin.

$^3$H-serotonin-labeled platelets were resuspended in Tyrode's buffer, pH 7.2, containing 100 μM EGTA (ethylene glycol bis(β-aminoethyl ether) N, N, N', N' tetraacetic acid) and no calcium. The platelets were then divided into three portions to which was added either 10 units/ml of PAF, 10 units/ml of 1-O-alkyl-2-acetyl-sn-glyceryl-3-phosphorylcholine (AGEPC), or albumin-saline as a control. Following incubation at 37° C. for 20 minutes the platelets were washed twice prior to resuspension in Tyrode's buffer, pH 7.2, containing $1.3 \times 10^{-3}$ M calcium. The desensitized and control platelets then were tested for their respective reactivity to 1.0 units of native PAF, 1-O-alkyl-2-acetyl-sn-glyceryl-3-phosphorylcholine, 1-acyl-2-acetyl-sn-glyceryl-3-phosphorylcholine (AcLL), calf skin collagen (25 μg/ml. Worthington Biochemical Co.) or thrombin (purified α-thrombin, 0.25 units/ml). Results were recorded as % $^3$H-serotonin release (mean±standard deviation).

| Test Stimulus | Desensitizing Agent | | |
|---|---|---|---|
| | Control | PAF | AGEPC |
| PAF | 50.4 ± 4.2 | 16.8 ± 9.6 | 16.8 ± 11.4 |
| AGEPC | 53.4 ± 0.3 | 15.7 ± 1.5 | 15.4 ± 6.1 |
| AcLL | 46.1 ± 5.4 | 12.1 ± 6.6 | 11.2 ± 6.6 |
| Collagen | 55.8 ± 4.3 | 57.5 ± 1.8 | 60.9 ± 11.1 |
| Thrombin | 64.3 ± 10.4 | 54.7 ± 9.3 | 66.6 ± 11.1 |

It can be seen that desensitization of platelets to native PAF also desensitized these cells to AGEPC and AcLL, but not to collagen or thrombin. In a similar fashion, desensitization of the platelets to AGEPC desensitized the platelets to AcLL and most importantly to native PAF. However, AGEPC did not desensitize platelets with respect to collagen or thrombin.

EXAMPLE 24

In addition to the desensitizing effects of AGEPC in vitro, Applicants have recently obtained evidence for AGEPC desensitization in vivo. Initially, it was demonstrated that during IgE-induced systemic anaphylaxis, the circulating platelets became desensitized to AGEPC. Subsequent studies demonstrated decreased neutrophil and platelet reactivity to AGEPC after repetitive challenge with AGEPC. Thus, an intravenous infusion of 1.21 μg AGEPC into rabbits resulted in the precipitous development of profound neutropenia, thrombocytopenia, and the release of significant amounts of platelet factor 4, PF4. Sixty minutes later, after the platelets and neutrophils had returned to the peripheral circulation and the PF4 levels had returned within preinfusion levels, a second dose of 1.21 μg AGEPC was administered. After the second AGEPC infusion there was a significant reduction in the amount of PF4 released, and the neutropenia was more transient and reversible than after a first injection of AGEPC. The reduced plasma levels of PF4 following the second injection of AGEPC could be ascribed to lowered PF4 content in the platelets due to initiation of release reaction following the first exposure to AGEPC.

EXAMPLE 25

To test this possibility, rabbits received mutiple infusions of 0.61 μg AGEPC every 60 minutes for a total of four infusions. Sixty minutes after the fourth infusion, 40.8 μg AGEPC (approximately 20 times a normally lethal dose) was infused. With each subsequent injection of 0.61 μg AGEPC, sequentially less PF4 was released into the plasma. However, following infusion of 40.8 μg AGEPC, substantial quantities of PF4 were released, indicating the platelets had adequate stores of PF4 and were capable of undergoing the release reaction following exposure to significantly elevated concentrations of AGEPC. These in vivo platelet secretion data therefore, were similar to the dose-response characteristics of the AGEPC-induced platelet desensitization that was demonstrated to occur in vitro. It was also interesting and significant that although severe respiratory and cardiovascular manifestations developed following the last infusion of 40.8 μg AGEPC, the rabbit survived the injection. In contrast, it had been Applicants' experience that doses exceeding 1.27 μg AGEPC routinely resulted in lethal reactions within 5 minutes. Thus, the series of multiple sublethal AGEPC infusions prevented a subsequent lethal reaction.

EXAMPLE 26

As a control for the preceding experiment, a relatively large dose (36.8 μg) of lyso-AGEPC was injected intravenously and as expected, there was no platelet changes, nor elevations in the plasma levels of PF4. In contrast to Example 25, the injection of 40.8 μg AGEPC resulted in an acute fatal reaction within 60 seconds of the AGEPC administration. These studies, therefore, demonstrate the protective effect of prior exposure to sublethal doses of AGEPC upon the subsequent reaction to a normally lethal dose of AGEPC. Applicants also observed that exposure of rabbits to repeated sublethal doses of AGEPC results in a subsequent diminution in both AGEPC-induced cardiovascular and pulmonary alterations.

EXAMPLE 27

AGEPC was utilized for systemic desensitization to prevent a clinically relevant disease. Experimental rabbits were rendered highly allergic to a specific antigen, horse radish peroxidase (HRP). If these rabbits at the age of 3 months are challenged intravenously with HRP they routinely develop a fatal systemic anaphylactic shock syndrome which includes the development of pulmonary hypertension, systemic hypotension and respiratory arrest. However by administering small quantities of AGEPC intravenously before administration of HRP, fatal anaphylaxis not only was prevented but none of the cardiovascular alterations developed. This prevention of anaphylaxis in the rabbit was accomplished by the continuous intravenous infusion of AGEPC (0.08 μg/kg body weight/minute for a two hour period) prior to intravenous antigen challenge with HRP. Such a challenge in a non-AGEPC desensitized rabbit would have resulted in death within 5–10 minutes as a result of pulmonary hypertension and systemic hypotension. In the desensitized rabbit none of these responses developed and the rabbit survived with normal cardiovascular physiology for two hours observed prior to terminating the experiment.

While the invention has been described in terms of preferred embodiments constituting the best mode known to the Applicants at the time of this application, various changes may be made in the invention without departing from the scope thereof which is defined by the following claims.

What is claimed is:

1. A method of therapeutic intervention to prevent systemic anaphylactic shock in a mammalian host susceptible to anaphylaxis upon challenge with an allergen, the method comprising:

determining that the host is susceptible to anaphylactic shock upon challenge with an allergen;

immediately prior to challenging the host with the allergen, administering to the host a sublethal, anti-anaphylactic effective amount of a compound represented by the formula:

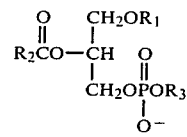

wherein
$R_1$ is a long chain carbon radical selected from the group consisting of $-(CH_2)_xCH_3$ and

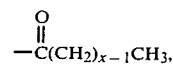

and x denotes the integer 15 or 17;
$R_2$ is methyl or ethyl or if $R_1$ is $-(CH_2)_xCH_3$ then $R_2$ can be n-propyl; and
$R_3$ is an amine selected from the group consisting of

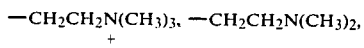

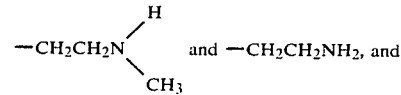

pharmaceutically acceptable salts thereof, and allowing the host to be challenged with the allergen, thereby preventing the systemic anaphylactic shock normally caused by the allergen.

2. The method according to claim 1 wherein the phosphoglyceride compound is represented by the formula:

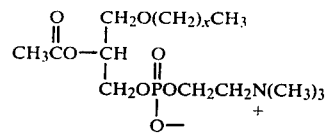

wherein x denotes the integer 15 or 17, and pharmaceutically acceptable salts thereof.

* * * * *